(12) United States Patent
Girdhar et al.

(10) Patent No.: US 11,963,713 B2
(45) Date of Patent: Apr. 23, 2024

(54) MEDICAL TREATMENT SYSTEM

(71) Applicant: Covidien LP, Mansfield, MA (US)

(72) Inventors: Gaurav Girdhar, Costa Mesa, CA (US); Hoai Nguyen, Westminster, CA (US)

(73) Assignee: Covidien LP, Mansfield, MA (US)

( * ) Notice: Subject to any disclaimer, the term of this patent is extended or adjusted under 35 U.S.C. 154(b) by 198 days.

(21) Appl. No.: 17/303,590

(22) Filed: Jun. 2, 2021

(65) Prior Publication Data
US 2022/0387098 A1 Dec. 8, 2022

(51) Int. Cl.
*A61B 18/14* (2006.01)
*A61B 18/00* (2006.01)
*A61B 18/12* (2006.01)

(52) U.S. Cl.
CPC ...... *A61B 18/1492* (2013.01); *A61B 18/1206* (2013.01); *A61B 2018/00077* (2013.01); *A61B 2018/00083* (2013.01); *A61B 2018/00148* (2013.01); *A61B 2018/0041* (2013.01)

(58) Field of Classification Search
CPC ............ A61B 18/1492; A61B 18/1206; A61B 2018/00077; A61B 2018/00083; A61B 2018/00148; A61B 2018/0041
See application file for complete search history.

(56) References Cited

U.S. PATENT DOCUMENTS

| 5,549,626 A | 8/1996 | Miller et al. |
| 5,928,260 A | 7/1999 | Chin et al. |
| 5,972,019 A | 10/1999 | Engelson et al. |
| 6,022,336 A | 2/2000 | Zadno-Azizi et al. |
| 6,059,779 A | 5/2000 | Mills |

(Continued)

FOREIGN PATENT DOCUMENTS

| CN | 101472685 A | 7/2009 |
| CN | 107405160 A | 11/2017 |

(Continued)

OTHER PUBLICATIONS

Extended European Search Report dated Jul. 15, 2021; European Application No. 18888795.4; 6 pages.

(Continued)

*Primary Examiner* — Linda C Dvorak
*Assistant Examiner* — Abigail Bock
(74) *Attorney, Agent, or Firm* — Fortem IP LLP

(57) ABSTRACT

Retrieval of material from vessel lumens can be improved by electrically enhancing attachment of the material to the removal device. The removal device can have a core assembly that includes a hypotube coupled to a first electrical terminal and a pushwire coupled to a second electrical terminal, the pushwire extending through the hypotube lumen. An insulating layer separates the hypotube and the pushwire, and an interventional element is coupled to a distal end of the pushwire. The interventional element can be disposed adjacent to a thrombus. An electrical signal is delivered to the interventional element to promote adhesion of the thrombus to the interventional element. The electrical signal can optionally be a periodic waveform, and the total energy delivered can be between 0.75-24,000 mJ and the peak current delivered via the electrical signal can be between 0.5-5 mA.

19 Claims, 7 Drawing Sheets

(56) References Cited

U.S. PATENT DOCUMENTS

| | | |
|---|---|---|
| 6,183,467 B1 | 2/2001 | Shapeton et al. |
| 6,315,794 B1 * | 11/2001 | Richter ................ A61F 2/915 |
| | | 623/1.34 |
| 6,540,733 B2 | 4/2003 | Constantz et al. |
| 6,658,288 B1 | 12/2003 | Hayashi |
| 6,663,650 B2 | 12/2003 | Sepetka et al. |
| 7,094,249 B1 | 8/2006 | Broome et al. |
| 7,520,966 B2 | 4/2009 | Diaz et al. |
| 7,556,624 B2 | 7/2009 | Laufer et al. |
| 8,038,674 B2 | 10/2011 | Schmaltz et al. |
| 8,246,641 B2 | 8/2012 | Osborne et al. |
| 8,382,821 B2 | 2/2013 | Richter |
| 8,603,014 B2 | 12/2013 | Alleman et al. |
| 8,795,305 B2 | 8/2014 | Martin et al. |
| 8,837,800 B1 | 9/2014 | Bammer et al. |
| 8,888,788 B2 | 11/2014 | Adams et al. |
| 8,965,534 B2 * | 2/2015 | Hyatt ................ A61N 1/0492 |
| | | 607/152 |
| 9,011,431 B2 | 4/2015 | Long et al. |
| 9,039,753 B2 | 5/2015 | Thramann |
| 9,119,656 B2 | 9/2015 | Bose et al. |
| 9,126,018 B1 | 9/2015 | Garrison |
| 9,179,971 B2 | 11/2015 | Kirschenman |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,681,882 B2 | 6/2017 | Wilson et al. |
| 9,713,730 B2 | 7/2017 | Mathur et al. |
| 9,737,318 B2 | 8/2017 | Monstadt et al. |
| 9,770,251 B2 | 9/2017 | Bowman et al. |
| 9,795,400 B2 | 10/2017 | Davidson |
| 9,801,643 B2 | 10/2017 | Hansen et al. |
| 9,808,271 B2 | 11/2017 | Ulm |
| 9,827,084 B2 | 11/2017 | Bonnette et al. |
| 9,861,783 B2 | 1/2018 | Garrison et al. |
| 9,901,543 B2 | 2/2018 | Chausson et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,092,241 B2 | 10/2018 | Toth et al. |
| 10,136,942 B1 | 11/2018 | Cosman |
| 10,251,569 B2 | 4/2019 | Burkett |
| 10,413,309 B2 | 9/2019 | Farhat et al. |
| 10,709,463 B2 | 7/2020 | Girdhar et al. |
| 10,847,411 B2 | 11/2020 | Chen et al. |
| 10,874,411 B2 | 12/2020 | Nguyen et al. |
| 10,987,117 B2 | 4/2021 | Girdhar et al. |
| 11,058,444 B2 | 7/2021 | Girdhar et al. |
| 11,090,071 B2 | 8/2021 | Girdhar et al. |
| 11,160,571 B2 | 11/2021 | Nguyen et al. |
| 11,666,350 B2 | 6/2023 | Nguyen et al. |
| 2001/0001314 A1 | 5/2001 | Davison et al. |
| 2002/0059938 A1 | 5/2002 | Fogarty et al. |
| 2002/0091407 A1 | 7/2002 | Zadno-Azizi et al. |
| 2002/0133111 A1 | 9/2002 | Shadduck et al. |
| 2003/0088245 A1 | 5/2003 | Woloszko et al. |
| 2004/0219660 A1 | 11/2004 | Dev et al. |
| 2005/0096647 A1 | 5/2005 | Steinke et al. |
| 2005/0228417 A1 | 10/2005 | Teitelbaum et al. |
| 2006/0089638 A1 | 4/2006 | Carmel et al. |
| 2008/0042662 A1 | 2/2008 | Abraham |
| 2008/0045881 A1 | 2/2008 | Teitelbaum et al. |
| 2008/0262489 A1 | 10/2008 | Steinke et al. |
| 2008/0294181 A1 | 11/2008 | Wensel et al. |
| 2009/0054918 A1 | 2/2009 | Henson |
| 2009/0069828 A1 | 3/2009 | Martin et al. |
| 2009/0240250 A1 | 9/2009 | Hayashi et al. |
| 2009/0318892 A1 | 12/2009 | Aboytes et al. |
| 2009/0318943 A1 | 12/2009 | Eidenschink et al. |
| 2009/0318994 A1 | 12/2009 | Eidenschink et al. |
| 2010/0004623 A1 | 1/2010 | Hamilton et al. |
| 2010/0010533 A1 | 1/2010 | Burke et al. |
| 2010/0042136 A1 | 2/2010 | Berrada et al. |
| 2010/0168739 A1 | 7/2010 | Wu et al. |
| 2010/0174309 A1 | 7/2010 | Fulkerson et al. |
| 2010/0228280 A1 | 9/2010 | Groothuis et al. |
| 2010/0256616 A1 | 10/2010 | Katoh et al. |
| 2010/0256627 A1 | 10/2010 | Ma et al. |
| 2011/0130756 A1 | 6/2011 | Everson et al. |
| 2011/0196478 A1 | 8/2011 | Torosoff |
| 2011/0202085 A1 | 8/2011 | Loganathan et al. |
| 2011/0301549 A1 | 12/2011 | Hartmann |
| 2011/0301594 A1 | 12/2011 | Orion et al. |
| 2013/0008780 A1 | 1/2013 | Andreacchi et al. |
| 2013/0030461 A1 | 1/2013 | Marks et al. |
| 2013/0072960 A1 | 3/2013 | Schneider et al. |
| 2013/0184702 A1 | 7/2013 | Neal et al. |
| 2013/0281788 A1 | 10/2013 | Garrison |
| 2013/0282084 A1 | 10/2013 | Mathur et al. |
| 2013/0345739 A1 | 12/2013 | Brady et al. |
| 2014/0025069 A1 | 1/2014 | Willard et al. |
| 2014/0025152 A1 | 1/2014 | Headley |
| 2014/0172001 A1 | 6/2014 | Becking et al. |
| 2014/0180139 A1 | 6/2014 | Millett et al. |
| 2014/0188127 A1 | 7/2014 | Dubrul et al. |
| 2014/0276074 A1 | 9/2014 | Warner |
| 2014/0276778 A1 | 9/2014 | McLawhorn et al. |
| 2014/0277013 A1 | 9/2014 | Sepetka et al. |
| 2014/0277079 A1 | 9/2014 | Vale et al. |
| 2014/0309673 A1 | 10/2014 | Dacuycuy et al. |
| 2014/0309675 A1 | 10/2014 | Maisano et al. |
| 2014/0343595 A1 | 11/2014 | Monstadt et al. |
| 2014/0364896 A1 | 12/2014 | Consigny |
| 2015/0112321 A1 | 4/2015 | Cadouri |
| 2015/0133990 A1 | 5/2015 | Davidson |
| 2015/0150672 A1 | 6/2015 | Ma |
| 2015/0164666 A1 | 6/2015 | Johnson et al. |
| 2015/0182740 A1 | 7/2015 | Mickelsen |
| 2015/0230820 A1 | 8/2015 | Turjman et al. |
| 2015/0297251 A1 | 10/2015 | Sos |
| 2015/0359547 A1 | 12/2015 | Vale et al. |
| 2016/0008003 A1 | 1/2016 | Kleshinski et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157843 A1 | 6/2016 | Dickson et al. |
| 2016/0157985 A1 | 6/2016 | Vo et al. |
| 2016/0199620 A1 | 7/2016 | Pokorney et al. |
| 2016/0228681 A1 | 8/2016 | Di Palma et al. |
| 2016/0228684 A1 | 8/2016 | Martin |
| 2016/0242661 A1 * | 8/2016 | Fischell ................ A61B 5/6852 |
| 2016/0296690 A1 | 10/2016 | Kume et al. |
| 2016/0302808 A1 | 10/2016 | Loganathan et al. |
| 2016/0331377 A1 | 11/2016 | Divino et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0128126 A1 | 5/2017 | Sunenshine et al. |
| 2017/0164963 A1 | 6/2017 | Goyal |
| 2017/0215902 A1 | 8/2017 | Leynov et al. |
| 2017/0215955 A1 | 8/2017 | Hancock et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2017/0367707 A1 | 12/2017 | Divino |

(56) References Cited

U.S. PATENT DOCUMENTS

| | | |
|---|---|---|
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0133436 A1 | 5/2018 | Garrison et al. |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0161514 A1 | 6/2018 | Rothenberg et al. |
| 2018/0161541 A1 | 6/2018 | Haldis et al. |
| 2018/0185614 A1 | 7/2018 | Garrison et al. |
| 2018/0200040 A1 | 7/2018 | Wasdyke et al. |
| 2018/0236221 A1 | 8/2018 | Opie et al. |
| 2018/0303595 A1 | 10/2018 | Opie et al. |
| 2018/0344970 A1 | 12/2018 | Kornowski et al. |
| 2019/0038438 A1 | 2/2019 | John et al. |
| 2019/0046119 A1 | 2/2019 | Oxley |
| 2019/0175199 A1* | 6/2019 | Girdhar .................. A61F 2/95 |
| 2019/0175200 A1 | 6/2019 | Girdhar et al. |
| 2019/0239910 A1 | 8/2019 | Brady et al. |
| 2019/0262069 A1 | 8/2019 | Taff et al. |
| 2019/0388097 A1 | 12/2019 | Girdhar et al. |
| 2019/0388107 A1 | 12/2019 | Girdhar et al. |
| 2019/0388111 A1 | 12/2019 | Nguyen et al. |
| 2019/0388112 A1* | 12/2019 | Nguyen ........... A61B 17/22032 |
| 2020/0054392 A1 | 2/2020 | Whiteley et al. |
| 2020/0129742 A1 | 4/2020 | Cope et al. |
| 2020/0297367 A1 | 9/2020 | Girdhar et al. |
| 2020/0297410 A1 | 9/2020 | Nguyen et al. |
| 2020/0390455 A1 | 12/2020 | Nguyen et al. |
| 2020/0390456 A1 | 12/2020 | Nguyen et al. |
| 2020/0390457 A1 | 12/2020 | Nageswaran et al. |
| 2020/0390458 A1 | 12/2020 | Nguyen et al. |
| 2021/0068853 A1 | 3/2021 | Nguyen et al. |
| 2021/0177427 A1 | 6/2021 | Nguyen et al. |
| 2021/0177442 A1 | 6/2021 | Girdhar et al. |
| 2021/0177446 A1 | 6/2021 | Girdhar et al. |
| 2021/0186540 A1 | 6/2021 | Taff et al. |
| 2021/0267612 A1 | 9/2021 | Girdhar et al. |
| 2022/0022899 A1 | 1/2022 | Girdhar et al. |
| 2022/0022900 A1 | 1/2022 | Nguyen et al. |
| 2022/0125455 A1 | 4/2022 | Girdhar et al. |
| 2022/0202431 A1 | 6/2022 | Davidson et al. |
| 2022/0218372 A1 | 7/2022 | Nguyen et al. |
| 2022/0387051 A1 | 12/2022 | Girdhar et al. |
| 2022/0409258 A1 | 12/2022 | Girdhar et al. |
| 2023/0064470 A1 | 3/2023 | Girdhar et al. |

FOREIGN PATENT DOCUMENTS

| | | |
|---|---|---|
| CN | 104884681 B | 5/2018 |
| EP | 1484025 A1 | 12/2004 |
| EP | 2319575 B1 | 11/2013 |
| EP | 2490764 B1 | 9/2014 |
| EP | 2895645 A1 | 7/2015 |
| EP | 2967605 A1 | 1/2016 |
| EP | 3184067 A1 | 6/2017 |
| JP | 10290805 A | 11/1998 |
| JP | 2014004219 A | 1/2014 |
| JP | 2018118132 A | 8/2018 |
| KR | 20180102877 A | 9/2018 |
| WO | 9724073 A1 | 7/1997 |
| WO | 0035363 A1 | 6/2000 |
| WO | 2009127037 A1 | 10/2009 |
| WO | 2010061376 A1 | 6/2010 |
| WO | 2014079148 A1 | 5/2014 |
| WO | 2015141317 A1 | 9/2015 |
| WO | 2016007388 A1 | 1/2016 |
| WO | 2016141025 A1 | 9/2016 |
| WO | 2016198947 A1 | 12/2016 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018127796 A1 | 7/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |
| WO | 2019102307 A1 | 5/2019 |
| WO | 2019118321 A1 | 6/2019 |
| WO | 2019246377 A2 | 12/2019 |
| WO | 2020174326 A1 | 9/2020 |

OTHER PUBLICATIONS

International Search Report and Written Opinion dated Feb. 26, 2021; International Application No. PCT/US20/63200; 14 pages.

International Search Report and Written Opinion dated May 25, 2020, International Application No. PCT/US20/22463, 10 pages.

International Search Report and Written Opinion dated Nov. 3, 2020, International Application No. PCT/US20/70142, 18 pages.

Fort, Stephen, et al., "'Fused-Gold' vs. 'Bare' stainless steel NIRflex stents of the same geometric design in diseased native coronary arteries. Long-term results from the NIR Top Study", Euro Interv 2007; 3:256-261.

International Search Report and Written Opinion dated Aug. 19, 2022, International Application No. PCT/US2022/031799, 12 pages.

International Search Report and Written Opinion dated Mar. 24, 2022; International Application No. PCT/US2021/061540; 10 pages.

* cited by examiner

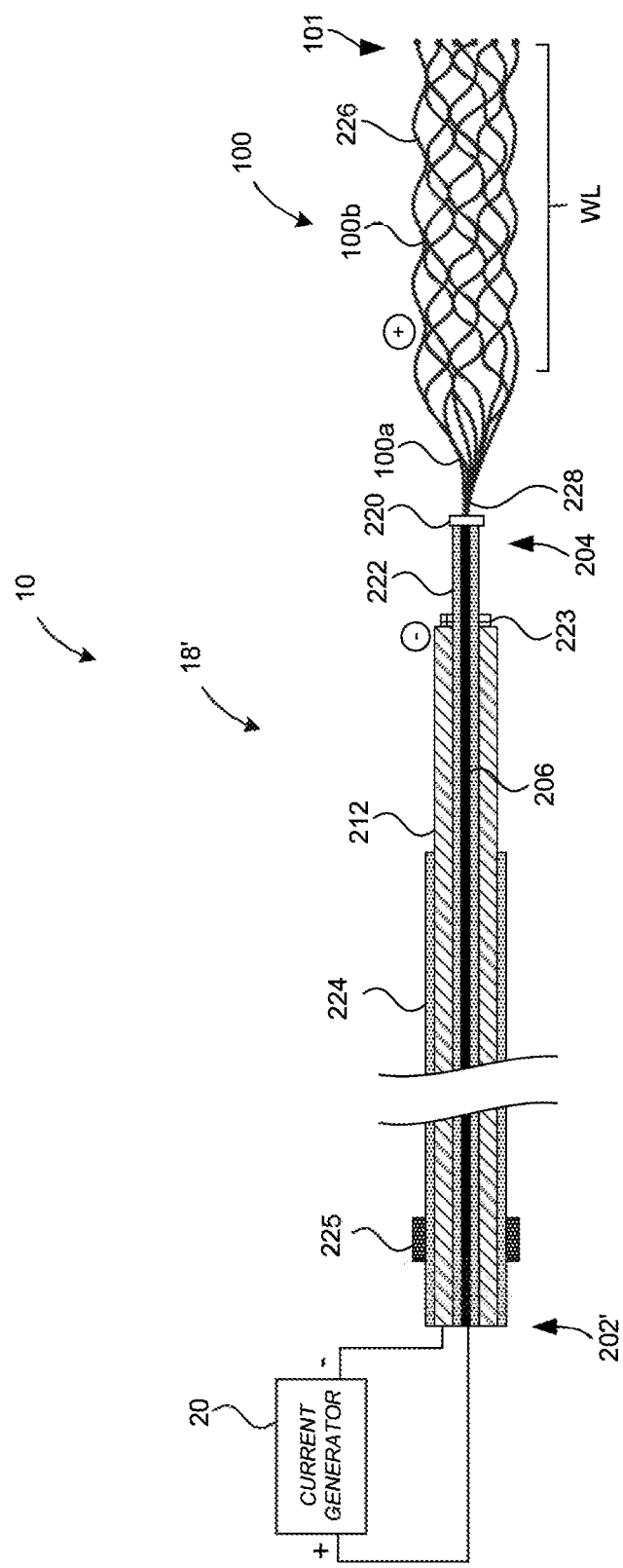

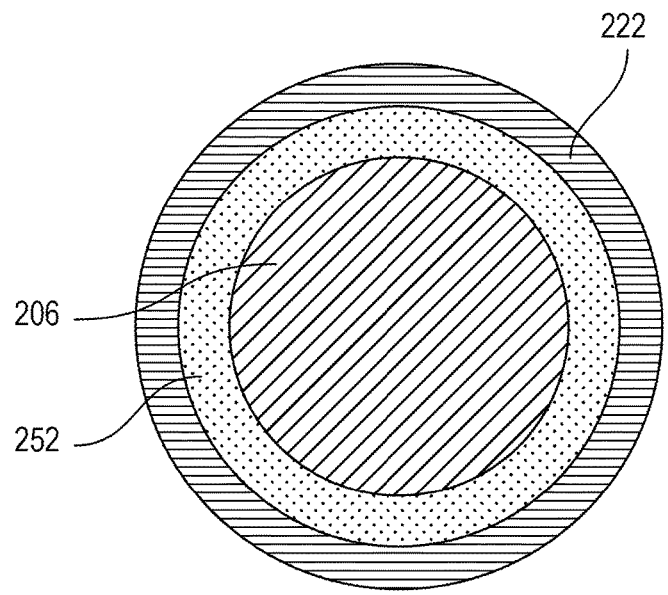
FIG. 3D
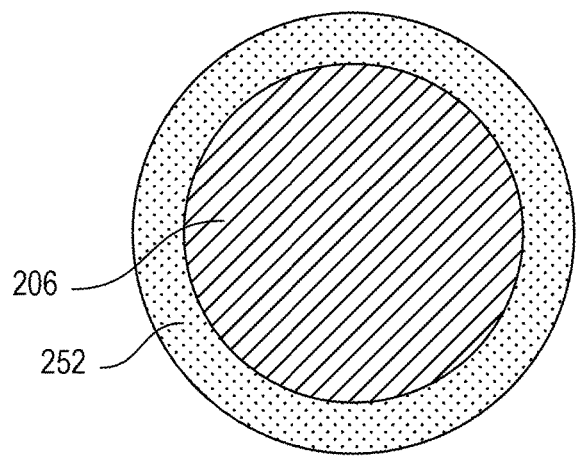 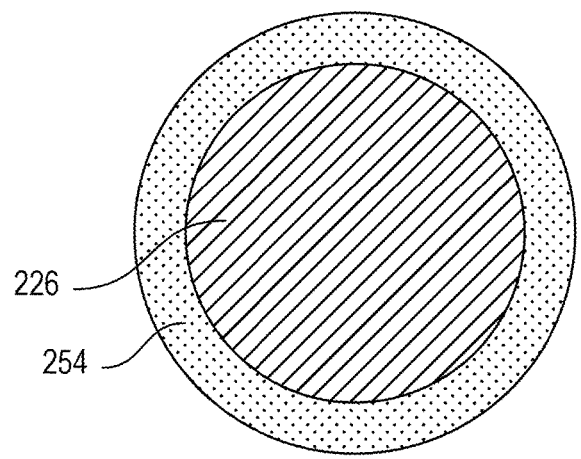
FIG. 3E  FIG. 3F

MEDICAL TREATMENT SYSTEM

TECHNICAL FIELD

The present technology relates generally to devices and methods for removing obstructions from body lumens. Some embodiments of the present technology relate to devices and methods for electrically enhanced removal of clot material from blood vessels.

BACKGROUND

Many medical procedures use medical devices to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages using this approach.

For example, one disadvantage is that the stent may not sufficiently retain the clot as it pulls the clot to the catheter. In such a case, some or all of the clot might remain the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (i.e., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial arterial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. If the interventional element can be made to exhibit positive charges (for example by application of direct current), there can be potential improvement in clot capture and retention and a reduced number of device passages or attempts to fully retrieve the clot. Embodiments of the present technology provide an interventional element with a positive electrical charge so as to attract negatively charged blood components, thereby improving attachment of the thrombus to the interventional element. The delivery electrode and return electrode can be integrated together into a multi-component or multi-channel core assembly coupled to the interventional element. A central conductive shaft or pushwire is coupled to the interventional element at its distal end, and a conductive tubular member or hypotube surrounds the pushwire along at least a portion of its length. The central pushwire can be coupled to a positive electrical terminal and the surrounding hypotube can be coupled to a negative electrical terminal. An electrically insulating layer can separate the central pushwire and the surrounding hypotube. An additional electrically insulating layer can surround the hypotube along a proximal portion, leaving a distalmost portion of the hypotube exposed so that the return circuit can be completed in the presence of blood or other electrolytic media. When voltage is applied at the terminals and the interventional element placed in the presence of blood (or any other electrolytic medium), current flows from the interventional element, through the blood, and to the distal portion of the hypotube which serves as the return electrode.

One approach to delivering current to an interventional element is to conduct current along a core assembly coupled to a proximal end of the interventional element. However, the inventors have discovered that this approach can lead to disadvantageous concentration of electrical charge along a proximal portion of the interventional element, with insufficient charge density in more distal portions of the interventional element (e.g., along some or all of the working length of the interventional element). This is particularly true of an interventional element having a proximal portion that tapers to a connection point with the core member. This concentration of current in the proximal portion can reduce the efficacy of electrostatic enhancement of clot adhesion, as the mechanical clot engagement occurs primarily at a location distal to the region at which the charge density is greatest. Additionally, when used in an aqueous chloride environment, such as the blood, hydrogen and chlorine gas bubbles can form along the surface of the interventional element in areas with high surface charge density (e.g., along a proximal portion of the interventional element). To reduce risk to the patient and ensure the treatment system functions properly, it may be beneficial to ensure that current flows through the entire interventional element, particularly ensuring sufficient current density in distal portions of the interventional element. When the entire interventional element exhibits a positive electrical charge, all portions of the interventional element can attract negatively charged blood components, thereby improving attachment of the thrombus to the interventional element. If portions of the interventional element are not positively charged (e.g., the distal portion is electrically neutral or exhibits insufficient charge density), those portions of the interventional element may not adequately attract negatively charged blood components, which can prevent improved attachment of the thrombus to the interventional element.

Embodiments of the present technology address these and other problems by providing an electrically conductive coating to one or more components of the treatment system. The conductive coating can be applied to an outer surface of the interventional element. By coating the interventional element with an electrically conductive material, current can easily be distributed through the interventional element instead of concentrating at the more proximal portions of the interventional element. Additionally or alternatively, a conductive coating can be applied to a distal end portion of the core assembly. The core assembly include an elongated tubular member, such as a hypotube, and can be positioned proximal the interventional element. Positioning the interventional element and core assembly in this manner, as well as applying a conductive coating to the core assembly and/or interventional element, encourages current to flow through all portions of the interventional element and thereby allows for the interventional element to reliably maintain a positive charge during treatment.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings. The subject technology is illustrated, for example, according to various aspects described below. These various aspects are provided as examples and do not limit the subject technology.

In one embodiment, a medical device is disclosed. The medical device can include a core assembly having a distal portion configured to be intravascularly positioned at a treatment site within a blood vessel lumen. The core assembly can include a hypotube operably coupled to a first electrical terminal, the hypotube having a proximal portion, a distal portion, and a lumen extending therethrough, the hypotube formed of a first conductive material; a second conductive material surrounding the distal portion of the hypotube along at least a portion of its length, the second conductive material having a higher electrically conductivity than the first conductive material; a pushwire operably coupled to a second electrical terminal, the pushwire extending through the hypotube lumen; an insulating material disposed radially between the hypotube and the pushwire, the insulating material extending from the proximal portion of the hypotube to the distal portion of the hypotube; and an interventional element coupled to a distal end of the pushwire, the interventional element having a body formed of a third conductive material and a coating of a fourth conductive material disposed over the third conductive material, the fourth conductive material having a higher electrical conductivity than the third material.

In some embodiments, the second conductive material and the fourth conductive material are the same. In some embodiments, the second conductive material and the fourth conductive material each comprises gold. In some embodiments, a proximal end of the interventional element is separated from a distal end of the hypotube by a distance of at least about 1 inch. In some embodiments, the second conductive material has a thickness of between about 0.05 microns and 5 microns. In some embodiments, the fourth conductive material has a thickness of between about 0.05 microns and 5 microns. In some embodiments, when the interventional element is in the presence of an electrolytic medium and voltage is supplied to the first and second electrical terminals, current flows from the fourth conductive material to the second conductive material.

In one embodiment, a medical device is disclosed. The medical device can include an elongated shaft having a proximal portion configured to be electrically coupled to a current generator, an intermediate portion at least partially covered with an insulative material, and a distal portion; an elongated tubular member having a proximal portion configured to be electrically coupled to the current generator, a distal portion, and a lumen receiving the elongated shaft therethrough, the elongated tubular member formed of a first conductive material; a second conductive material surrounding the distal portion of the elongated shaft along at least a portion of its length, the second conductive material having a higher electrical conductivity than the first conductive material; an interventional element coupled to the distal portion of the elongated shaft, the interventional element comprising a body formed of a third conductive material; and a fourth conductive material disposed over the third conductive material, the fourth conductive material having a higher electrical conductivity than the third material.

In some embodiments, the second conductive material and the fourth conductive material are the same. In some embodiments, the second conductive material and the fourth conductive material each comprises gold. In some embodiments, a proximal end of the interventional element is separated from a distal end of the elongated tubular member by a distance of at least about 1 inch. In some embodiments, the second conductive material has a thickness of between about 0.05 microns and 5 microns. In some embodiments, the fourth conductive material has a thickness of between about 0.05 microns and 5 microns. In some embodiments, when the interventional element is in the presence of an electrolytic medium and voltage is supplied to the elongated shaft and the elongated tubular member, current flows from the fourth conductive material to the second conductive material.

In one embodiment, a method for delivering an electrical current to a treatment device is described. The method can include inserting a treatment device into a patient. The treatment device can include: an elongated shaft having a proximal portion configured to be electrically coupled to a current generator, an intermediate portion at least partially covered with an insulative material, and a distal portion; an elongated tubular member having a proximal portion configured to be electrically coupled to the current generator, a distal portion, and a lumen receiving the elongated shaft therethrough, the elongated tubular member formed of a first conductive material; a second conductive material surrounding the distal portion of the elongated shaft along at least a portion of its length, the second conductive material having a higher electrical conductivity than the first conductive material; an interventional element coupled to the distal portion of the elongated shaft, the interventional element comprising a body formed of a third conductive material; and a fourth conductive material disposed over the third conductive material, the fourth conductive material having a higher electrical conductivity than the third material. The method can further include positioning the treatment device proximate a thrombus within a lumen of a blood vessel at a treatment site; and delivering an electrical current to the treatment device.

In some embodiments, the second conductive material and the fourth conductive material are the same. In some embodiments, the second conductive material and the fourth conductive material each comprises gold. In some embodiments, a proximal end of the interventional element is separated from a distal end of the elongated tubular member by a distance of at least about 1 inch. In some embodiments, the second conductive material has a thickness of between about 0.05 microns and 5 microns. In some embodiments, the fourth conductive material has a thickness of between about 0.05 microns and 5 microns.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 2B shows a side schematic cross-sectional view of a treatment system in accordance with one or more embodiments of the present technology.

FIG. 3D shows a cross-sectional view of a portion of an elongated shaft with an insulative material in accordance with one or more embodiments of the present technology.

FIG. 3E shows a cross-sectional view of a portion of an elongated shaft in accordance with one or more embodiments of the present technology.

FIG. 3F shows a cross-sectional view of a portion of an interventional element in accordance with one or more embodiments of the present technology.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the retrieval devices of the present technology may be used to remove emboli from body lumens other than blood vessels (e.g., the digestive tract, etc.) and/or may be used to remove emboli from blood vessels outside of the brain (e.g., pulmonary blood vessels, blood vessels within the legs, etc.). In addition, the retrieval devices of the present technology may be used to remove luminal obstructions other than clot material (e.g., plaque, resected tissue, foreign material, etc.).

Figure 1A:
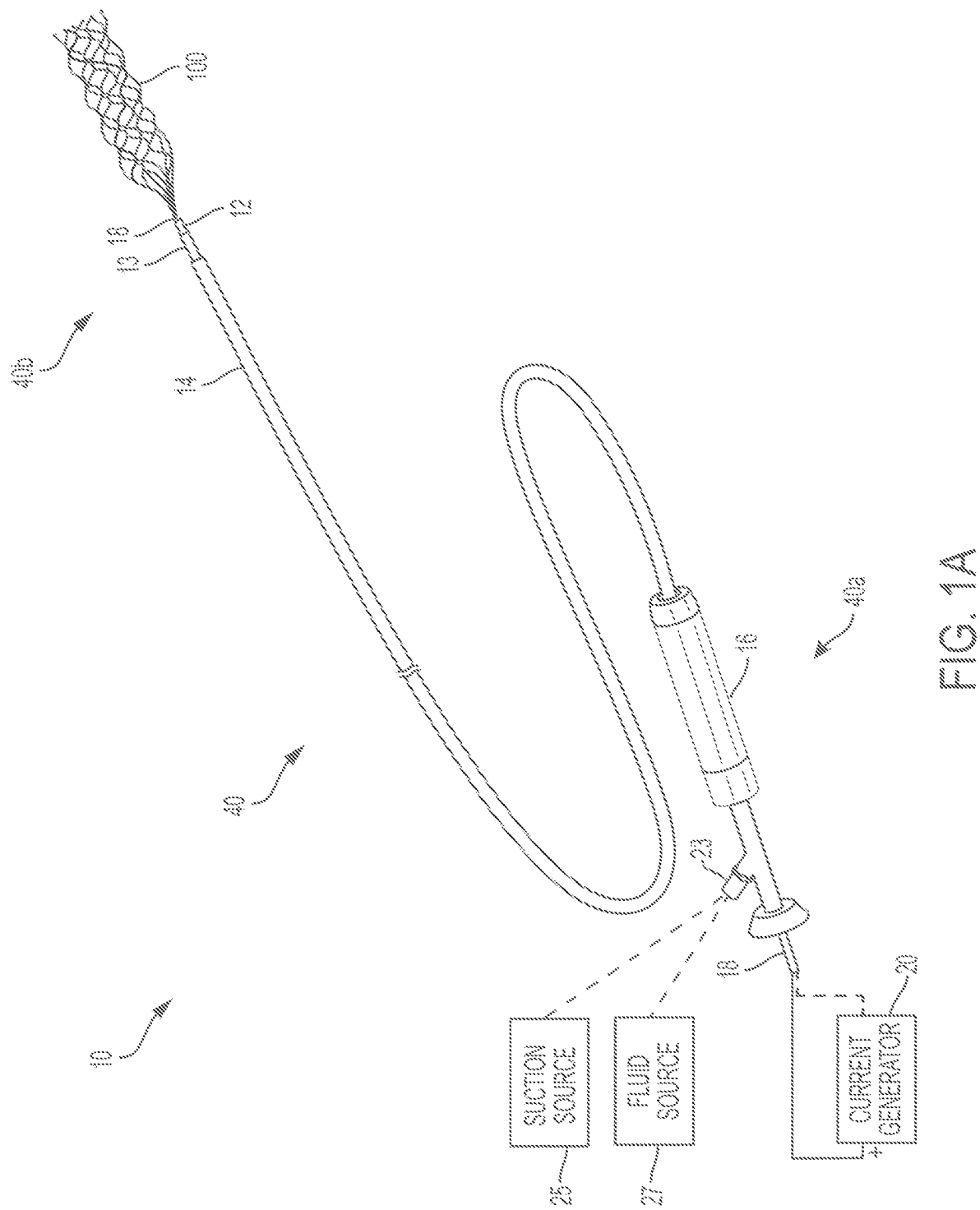
FIG. 1A shows a perspective view of an electrically enhanced treatment system for retrieving material from a body lumen, in accordance with one or more embodiments of the present technology.

FIG. 1A illustrates a view of an electrically enhanced treatment system 10 according to one or more embodiments of the present technology. As shown in FIG. 1A, the treatment system 10 can include a current generator 20 and a treatment device 40 having a proximal portion 40a configured to be coupled to the current generator 20 and a distal portion 40b configured to be intravascularly positioned within a blood vessel (such as an intracranial blood vessel) at a treatment site at or proximate a thrombus. The treatment device 40 includes an interventional element 100 at the distal portion 40b, a handle 16 at the proximal portion 40a, and a plurality of elongated shafts or members extending therebetween. For example, in some embodiments, such as that shown in FIG. 1A, the treatment device 40 includes a first catheter 14 (such as a balloon guide catheter), a second catheter 13 (such as a distal access catheter or aspiration catheter) configured to be slidably disposed within a lumen of the first catheter 14, a third catheter 12 (such as a microcatheter) configured to be slidably disposed within a lumen of the second catheter 13, and a core assembly 18 configured to be slidably disposed within a lumen of the third catheter 12. In some embodiments, the treatment device 40 does not include the second catheter 13. The first catheter 14 can be coupled to the handle 16, which provides proximal access to the core assembly 18 that engages the interventional element 100 at a distal end thereof. The current generator 20 may be coupled to a proximal portion of one or more leads (not shown) to deliver electrical current to the interventional element 100 and thereby provide an electrically charged environment at the distal portion 40b of the treatment device 40, as described in more detail below.

In some embodiments, the treatment system 10 includes a suction source 25 (e.g., a syringe, a pump, etc.) configured to be fluidically coupled (e.g., via a connector 23) to a proximal portion of one or more of the first catheter 14, the second catheter 13, and/or the third catheter 12 to apply negative pressure therethrough. In some embodiments, the treatment system 10 includes a fluid source 27 (e.g., a fluid reservoir, a syringe, pump, etc.) configured to be fluidically coupled (e.g., via the connector 23) to a proximal portion of one or more of the first catheter 14, the second catheter 13, and/or the third catheter 12 to supply fluid (e.g., saline, contrast agents, a drug such as a thrombolytic agent, etc.) to the treatment site.

According to some embodiments, the catheters 12, 13, and 14 can each be formed as a generally tubular member extending along and about a central axis. According to some embodiments, the third catheter 12 is generally constructed to track over a conventional guidewire in the cervical anatomy and into the cerebral vessels associated with the brain and may also be chosen according to several standard designs that are generally available. Accordingly, the third catheter 12 can have a length that is at least 125 cm long, and more particularly may be between about 125 cm and about 175 cm long. Other designs and dimensions are contemplated.

The second catheter 13 can be sized and configured to slidably receive the third catheter 12 therethrough. As noted above, the second catheter 13 can be coupled at a proximal portion to a suction source 25 (FIG. 1A) such as a pump or syringe in order to supply negative pressure to a treatment site. The first catheter 14 can be sized and configured to slidably receive both the second catheter 13 and the third catheter 12 therethrough. In some embodiments, the first catheter 14 is a balloon guide catheter having an inflatable balloon or other expandable member surrounding the catheter shaft at or near its distal end. In operation the first catheter 14 can first be advanced through a vessel and then its balloon can be expanded to anchor the first catheter 14 in place and/or arrest blood flow from areas proximal of the balloon, e.g. to enhance the effectiveness of aspiration performed via the first catheter 14 and/or other catheter(s). Next, the second catheter 13 can be advanced through the first catheter 14 until its distal end extends distally beyond the distal end of the first catheter 14. The second catheter 13 can be positioned such that its distal end is adjacent a treatment site (e.g., a site of a blood clot within the vessel). The third catheter 12 may then be advanced through the second catheter 13 until its distal end extends distally beyond the distal end of the second catheter 13. The interventional element 100 may then be advanced through the third catheter 12 for delivery to the treatment site.

According to some embodiments, the bodies of the catheters 12, 13, and 14 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

Figure 1B:
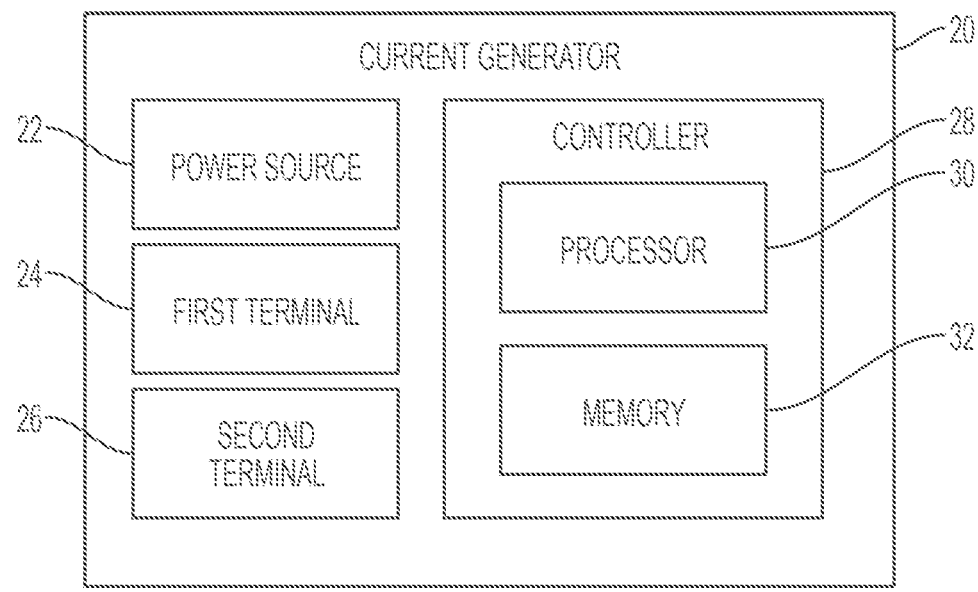
FIG. 1B shows a schematic view of a current generator, in accordance with one or more embodiments of the present technology.
Figure 1C:
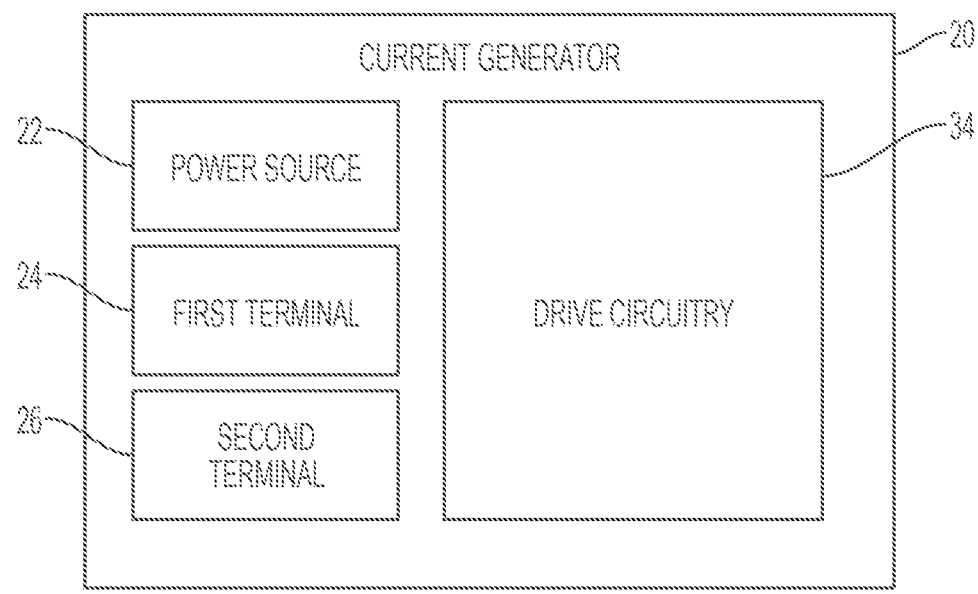
FIG. 1C shows a schematic view of a current generator, in accordance with one or more embodiments of the present technology.

According to some embodiments, the current generator 20 can include an electrical generator configured to output medically useful electric current. FIGS. 1B and 1C are schematic views of different embodiments of the current generator 20. With reference to FIG. 1B, the current generator 20 can include a power source 22, a first terminal 24, a second terminal 26, and a controller 28. The controller 28 includes a processor 30 coupled to a memory 32 that stores instructions (e.g., in the form of software, code or program instructions executable by the processor or controller) for causing the power source 22 to deliver electric current according to certain parameters provided by the software, code, etc. The power source 22 of the current generator 20 may include a direct current power supply, an alternating current power supply, and/or a power supply switchable between a direct current and an alternating current. The current generator 20 can include a suitable controller that can be used to control various parameters of the energy output by the power source or generator, such as intensity, amplitude, duration, frequency, duty cycle, and polarity. For example, the current generator 20 can provide a voltage of about 2 volts to about 28 volts and a current of about 0.5 mA to about 20 mA.

FIG. 1C illustrates another embodiment of the current generator 20, in which the controller 28 of FIG. 1B is replaced with drive circuitry 34. In this embodiment, the current generator 20 can include hardwired circuit elements to provide the desired waveform delivery rather than a software-based generator of FIG. 1B. The drive circuitry 34 can include, for example, analog circuit elements (e.g., resistors, diodes, switches, etc.) that are configured to cause the power source 22 to deliver electric current via the first and second terminals 24, 26 according to the desired parameters. For example, the drive circuitry 34 can be configured to cause the power source 22 to deliver periodic waveforms via the first and second terminals 24, 26.

In some embodiments, the endovascular delivery of electrical current requires the use of a negative electrode (and/or associated negative conductive path) that is wholly separated from the positive electrode (and/or associated positive conductive path). This may involve, for example, the use of a negative electrode embedded within a catheter wall, or a needle puncturing the patient to complete a conductive pathway. In various embodiments, the positive electrode (and/or associated positive conductive path) and the negative electrode (and/or associated negative conductive path) can be integrated in a core assembly and separated by an insulating material. Thus, according to one or more aspects of the present technology, electrically enhanced endovascular material removal can be facilitated by an electrode pair and associated positive and negative conductive paths provided within a treatment system, thereby avoiding the need to insert a needle into the patient to complete a circuit through the patient's tissue.

Figure 2A:
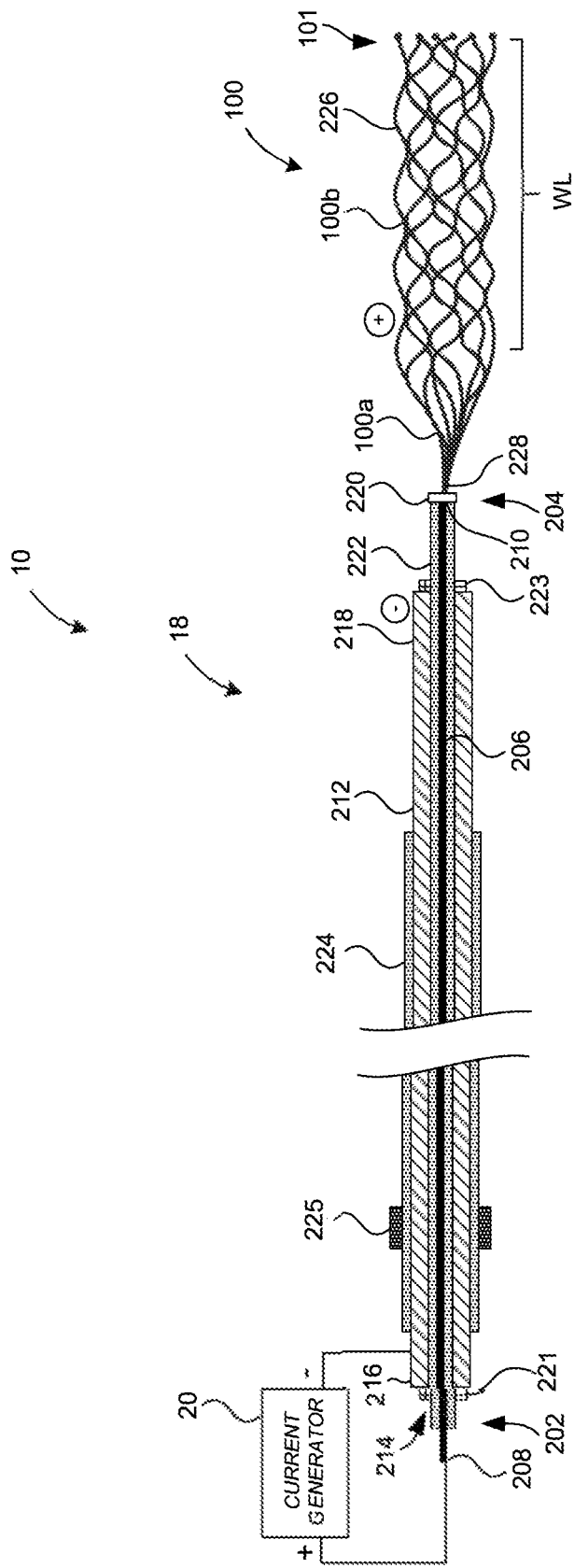
FIG. 2A shows a side schematic cross-sectional view of a treatment system for retrieving material from a body lumen in accordance with one or more embodiments of the present technology.

FIG. 2A is a side schematic cross-sectional view of a treatment system 10 in accordance with one or embodiments of the present disclosure. The treatment system 10 includes the current generator 20, the core assembly 18, and the interventional element 100. As illustrated, the current generator 20 is electrically coupled to a proximal portion 202 of the core assembly 18, and the interventional element 100 is coupled to a distal portion 204 of the core assembly 18.

In some embodiments, the core assembly 18 can include multiple (e.g., two, or more than two) separate conductive paths or channels that provide electrical communication along the core assembly 18 with a corresponding number (e.g., two, or more than two) electrodes of the treatment system 10. The interventional element 100 can serve as one electrode (e.g., the delivery electrode) in electrical communication with one of the conductive paths of the core assembly 18. Another of the conductive paths of the core assembly 18 can be in electrical communication with another electrode (e.g., a return electrode) which can optionally form part of the core assembly 18. The various embodiments of the core assembly 18 can be sized for insertion into a bodily lumen, such as a blood vessel, and can be configured to push and pull a device such as the interventional element 100 along the bodily lumen.

In some embodiments, as seen for example in FIG. 2A, the core assembly 18 includes an elongate conductive shaft 206 and an elongate tubular member 212 having a lumen 214 through which the shaft 206 extends. The shaft 206 has a proximal portion 208 and a distal portion 210, and the tubular member 212 has a proximal portion 216 and a distal portion 218. Both the shaft 206 and the tubular member 212 are electrically conductive along their respective lengths. In some embodiments, the positions of the shaft 206 and the tubular member 212 are fixed relative to one another. For example, in some embodiments the shaft 206 is not slidable or rotatable with respect to the tubular member 212 such that the core assembly 18 can be pushed or pulled without relative movement between the shaft 206 and the tubular member 212 and/or other individual components of the core assembly 18.

In some embodiments, the shaft 206 can be a solid pushwire, for example a wire made of Nitinol or other metal or alloy. The shaft 206 may be thinner than would otherwise be required due to the additional structural column strength provided by the surrounding tubular member 212. The tubular member 212 can be a hollow wire, hypotube, braid, coil, or other suitable member(s), or a combination of wire(s), tube(s), braid(s), coil(s), etc. In some embodiments, the tubular member 212 can be a laser-cut hypotube having a spiral cut pattern along at least a portion of its length. The tubular member 212 can be made of stainless steel (e.g., 304 SS), Nitinol, and/or other alloy. In at least some embodiments, the tubular member 212 can have a laser cut pattern to achieve the desired mechanical characteristics (e.g., column strength, flexibility, kink-resistance, etc.).

The core assembly 18 can also include an adhesive or a mechanical coupler such as a crimped band or marker band 220 disposed at the distal end of the core assembly 18, and the marker band 220 can optionally couple the distal end of the core assembly 18 to the interventional element 100. The marker band 220 can be radiopaque, for example including platinum or other radiopaque material, thereby enabling visualization of the proximal end of the interventional element 100 under fluoroscopy. In some embodiments, additional radiopaque markers can be disposed at various locations along the treatment system 10, for example along the shaft 206, the tubular member 212, or the interventional element 100 (e.g., at the distal end of the interventional element 100). The core assembly 18 can further include a proximal restraint 221 and/or a distal restraint 223 that are configured to maintain the relative positions of the elongate tubular member 212 and the shaft 206. The proximal restraint 221 is positioned at or near the proximal end of the tubular member 212, and the distal restraint 223 can be positioned at or near the distal end of the tubular member 212. In some embodiments, the proximal and distal restraints 221, 223 comprise adhesive disposed radially around the shaft 206 such that the tubular member 208 cannot slide longitudinally with respect to the shaft 206. In other embodiments, the proximal and/or distal restraints 221, 223 can be crimped bands or other suitable structures that limit longitudinal movement of the tubular member 212 with respect to the shaft 206. In at least some embodiments, the proximal and/or distal restraints 221, 223 can be radiopaque.

In at least some embodiments, the core assembly 18 also includes a first insulating layer or material 222 extending between the shaft 206 and the surrounding tubular member 212. The first insulating material 222 can be, for example, PTFE (polytetrafluoroethylene or TEFLON™) or any other suitable electrically insulating coating (e.g., polyimide, oxide, ETFE based coatings, or any suitable dielectric polymer). In some embodiments, the first insulating material 222 extends along substantially the entire length of the shaft 206. In some embodiments, the first insulating material 222 separates and electrically insulates the shaft 206 and the tubular member 212 along the entire length of the tubular member 212. In the embodiment illustrated in FIG. 2A, the first insulating material 222 does not cover the proximal-most portion of the shaft 206, providing an exposed region of the shaft 206 to which the current generator 20 can be electrically coupled. In some embodiments, for example as illustrated in FIG. 2B, the first insulating material 222 terminates proximally at the proximal terminus of the shaft 206, and the current generator 20 can electrically couple to the shaft 206 at its proximal terminus, for example using a coaxial connector.

The core assembly 18 can additionally include a second insulating layer or material 224 surrounding the tubular member 212 along at least a portion of its length. The second insulating layer 224 can be, for example, PTFE or any other suitable electrically insulative coating (e.g., polyimide, oxide, ETFE based coatings or any suitable dielectric polymer). In some embodiments, the distal portion 218 of the tubular member 212 is not covered by the second insulating layer 224, leaving an exposed conductive surface at the distal portion 218. In some embodiments, the length of the exposed distal portion 218 of the tubular member 212 can be at least (or equal to) 1, 2, 3, 4, 5, 6, or more inches. In some embodiments, the length of the exposed distal portion 218 of the tubular member 212 can be between at least 1 and 10 inches, or between 2 inches and 8 inches, or between 3 and 7 inches, or between 4 and 6 inches, or about 5 inches. This exposed portion of the distal portion 218 of the tubular member 212 provides a return path for current supplied to the delivery electrode (e.g. the entirety or a portion of the interventional element 100). As will be described in more detail, in some embodiments, a conductive material 250 can couple to the tubular member 212 at the exposed distal portion 218. In the embodiment illustrated in FIG. 2A, the second insulating material 224 does not cover the proximal-most portion of the tubular member 212, providing an exposed region of the tubular member 212 to which the current generator 20 can be electrically coupled. In some embodiments, for example as illustrated in FIG. 2B, the second insulating material 224 proximally terminates at the proximal end of the proximal terminus of the tubular member 212, and the current generator 20 can electrically couple to the tubular member 212 at its proximal terminus, for example using a coaxial connector.

The core assembly 18 can also include a retraction marker 225 in the proximal portion 216 of the tubular member 212. The retraction marker 225 can be a visible indicator to guide a clinician when proximally retracting an overlying catheter with respect to the core assembly 18. For example, the retraction marker 225 can be positioned such that when a proximal end of the overlying catheter is retracted to be positioned at or near the retraction marker 225, the distal portion 218 of the tubular member 212 is positioned distally beyond a distal end of the catheter. In this position, the exposed distal portion 218 of the tubular member 212 is exposed to the surrounding environment (e.g., blood, tissue, etc.), and can serve as a return electrode for the core assembly 18.

The proximal end 208 of the shaft 206 can be electrically coupled to the positive terminal of the current generator 20, and the proximal end of the tubular member 212 can be electrically coupled to the negative terminal of the current generator 20. During operation, the treatment system 10 provides an electrical circuit in which current flows from the positive terminal of the current generator 20, distally through the shaft 206, the interventional element 100, and the surrounding media (e.g., blood, tissue, thrombus, etc.) before returning back to the exposed distal portion 218 of the tubular member, proximally through the tubular member 212, and back to the negative terminal of the current generator 20.

As noted above, the current generator 20 can include a power source and either a processor coupled to a memory that stores instructions for causing the power source to deliver electric current according to certain parameters, or hardwired circuit elements configured to deliver electric current according to the desired parameters. The current generator 20 may be integrated into the core assembly 18 or may be removably coupled to the core assembly 18, for example via clips, wires, plugs or other suitable connectors.

In certain embodiments, the polarities of the current generator 20 can be switched, so that the negative terminal is electrically coupled to the shaft 206 and the positive terminal is electrically coupled to the tubular member 212. This can be advantageous when, for example, attempting to attract predominantly positively charged material to the interventional element 100, or when attempting to break up a clot rather than grasp it with an interventional element. In some embodiments alternating current (AC) signals may be used rather than DC. In certain instances, AC signals may advantageously help break apart a thrombus or other material.

In the illustrated embodiments of FIGS. 2A-2B, the interventional element 100 can be a thrombectomy device having a low-profile configuration (not shown) when constrained within a delivery catheter (e.g., a microcatheter) and an expanded configuration for securing and/or engaging clot material or other obstructions within a blood vessel lumen (e.g., a cerebral blood vessel lumen) and/or for restoring blood flow within the blood vessel. The interventional element 100 has a proximal portion 100a coupled to the shaft 206 and a distal portion 100b. The interventional element 100 further includes an open cell framework or body 226 and a coupling region 228 extending proximally from the body 226. In some embodiments, a distal portion 100b of the interventional element 100 can be generally tubular (e.g., cylindrical), and the proximal portion 100a of the interventional element 100 can taper proximally to the coupling region 228. In various embodiments, the interventional element 100 can take any number of forms, for example a removal device, a thrombectomy device, a stent retriever, a stent, or other suitable medical device. For example, in some embodiments the interventional element 100 is a mesh structure formed of a superelastic material (e.g., Nitinol) or other resilient or self-expanding material configured to self-expand when released from the delivery catheter. The interventional element can be a metallic or electrically conductive thrombectomy device having a number of struts and open spaces between the struts, and the struts and spaces can be situated along the longitudinal direction of the interventional element, the radial direction, or both. For example, in some embodiments the interventional element 100 may be a stent and/or stent retriever, such as Medtronic's Solitaire™ Revascularization Device, Stryker Neurovascular's Trevo® ProVue™ Stentriever, or other suitable devices. In other embodiments, the interventional element 100 may include a plurality of braided filaments. Examples of suitable interventional elements 100 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The interventional element 100 can be characterized by a working length WL, which can correspond to the region of the interventional element 100 configured to engage a thrombus or other material to be removed from a vessel lumen. In some embodiments, the non-working length portion of the interventional element 100 (i.e., proximal portion 100a) can be coated with a non-conductive material (e.g., PTFE or other suitable non-conductive coating) such that the coated region is not in electrical contact with the surrounding media (e.g., blood). As a result, the current carried by the shaft 206 to the interventional element 100 is only exposed to the surrounding media in the working length WL portion of the interventional element 100. This can advantageously concentrate the electrically enhanced attachment effect along the working length WL of the interventional element 100, where it is most useful, and thereby combine both the mechanical interlocking provided by the working length WL/body 226 and the electrical enhancement provided by the delivered electrical signal. In some embodiments, a distal region of the interventional element 100 may likewise be coated with a non-conductive material (e.g., PTFE or other suitable non-conductive coating), leaving only a central portion of the interventional element 100 having an exposed conductive surface. As will be described in more detail, in some embodiments, some or all of the interventional element 100 can be coated with a conductive material 252.

Figure 3A:
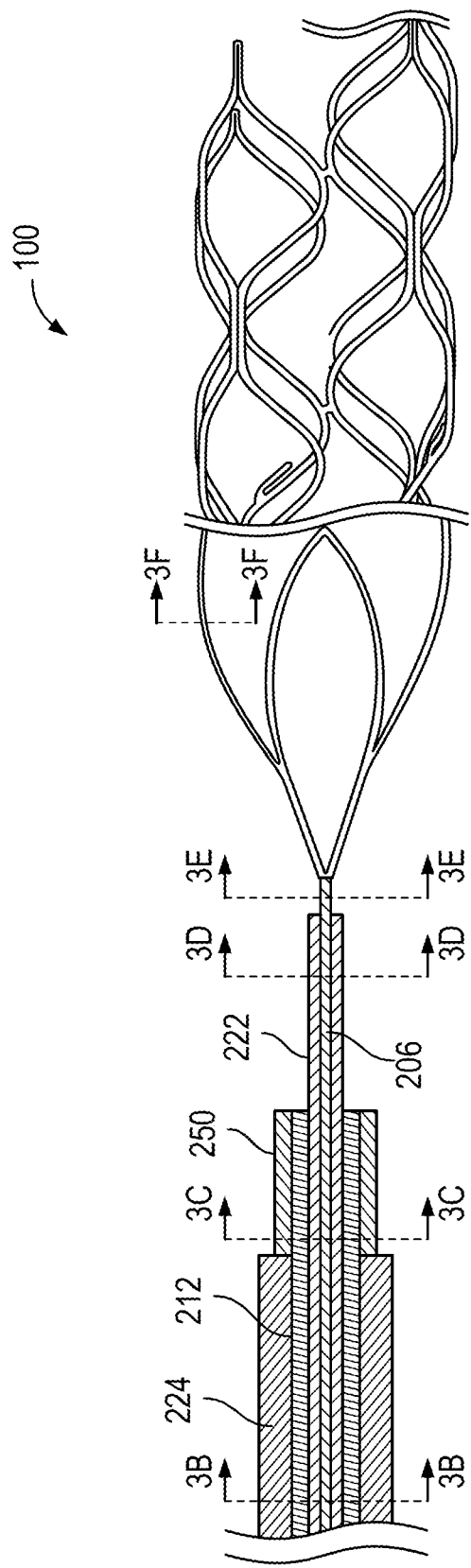
FIG. 3A shows a side schematic view of the treatment device for retrieving material from a body lumen in accordance with one or more embodiments of the present technology.
Figure 3B:
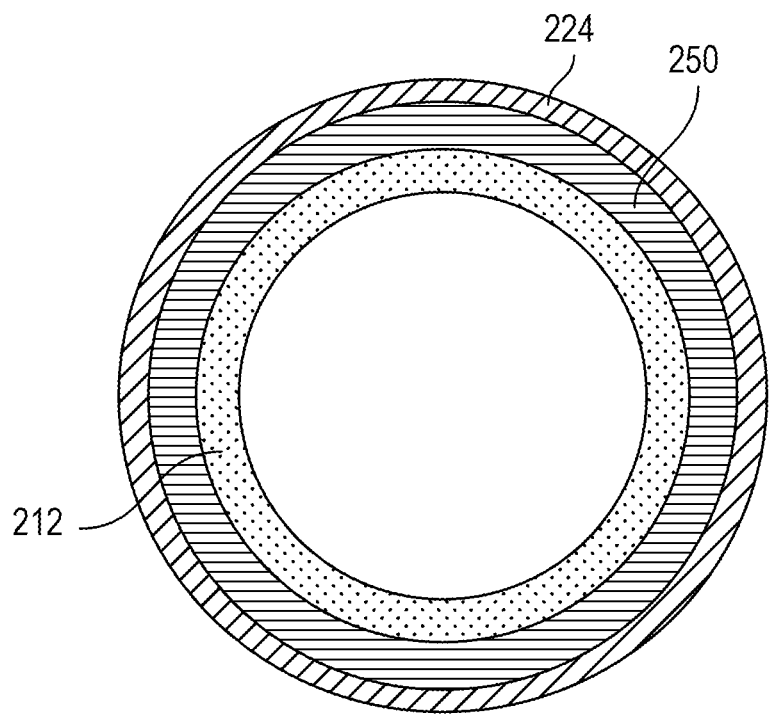
FIG. 3B shows a cross-sectional view of a portion of an elongated tubular member with an insulative material in accordance with one or more embodiments of the present technology.
Figure 3C:
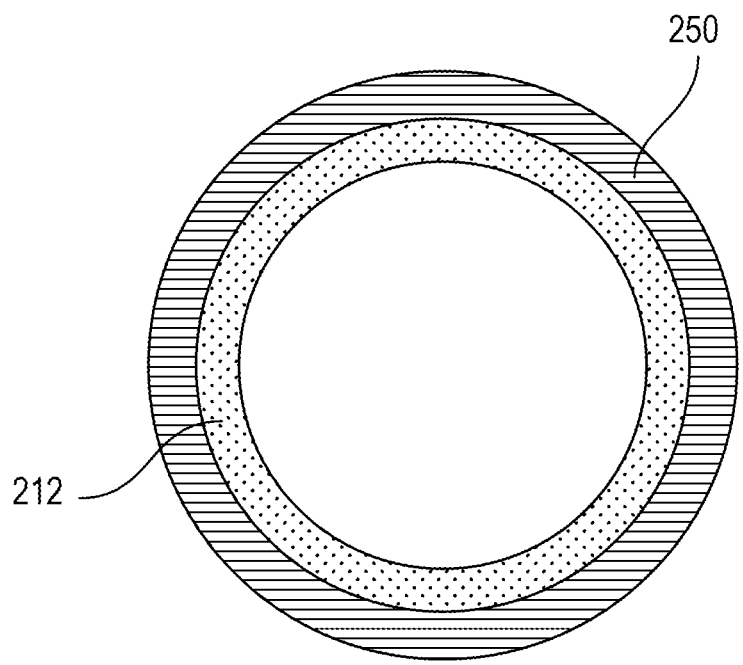
FIG. 3C shows a cross-sectional view of an elongated tubular member in accordance with one or more embodiments of the present technology.

FIG. 3A illustrates a side schematic view of the distal portion of the core assembly 18, with a portion of the core assembly 18 shown as a cross-sectional view for clarity. FIGS. 3B and 3C illustrate two cross-sectional views of the distal portion 218 of the tubular member 212 along the lines 3B and 3C in FIG. 3A, respectively, with a portion of the core assembly 18 hidden for clarity. FIGS. 3D and 3E illustrate two cross-sectional views of the distal portion of the shaft 206 along the lines 3D and 3E of FIG. 3A, respectively. FIG. 3F illustrates a cross-section view of the interventional element 100 along the line 3F of FIG. 3A. As illustrated in FIG. 3A, the shaft 206 extends through the lumen formed by the tubular member 212 such that the distal end portion of the shaft 206 extends distally from the distal end portion of the tubular member 212. In some embodiments, the shaft 206 can extend distally from the distal end of the tubular member 212 by a length of at least (or equal to) 1, 2, 3, 4, 5, 6, or more inches. As noted previously, a first insulating material 222 can surround the shaft 206 along at least a part of its length such that the first insulating material 222 is radially disposed between the shaft 206 and the tubular member 212. Additionally, the second insulating material 224 can surround an outer surface of the tubular member 212 along at least a part of the length of the tubular member 212. The interventional element 100 can couple to the distal end portion of the shaft 206 and extend distally from the tubular member 212. In some embodiments, the interventional element 100 is separated from the distal end of the tubular member 212 by a length of at least (or equal to) 1, 2, 3, 4, 5, 6, or more inches.

According to some embodiments, a conductive material 250 can be coupled to the tubular member 212 along at least a portion of the length of the tubular member 212. The conductive material 250 can be disposed over an outer surface of the tubular member 212 so that the conductive material 250 surrounds the outer surface of the tubular member 212. For example, as illustrated in FIG. 3C, the conductive material 250 can be coupled to the outer surface of the tubular member 212 so that the conductive material 250 surrounds the tubular member 212. As noted previously, one or more portions of the tubular member 212 can be uninsulated, exposing the outer surface of the tubular member 212. In some embodiments, the conductive material 250 can couple to the tubular member 212 at these uninsulated portions of the tubular member 212. For example, as illustrated in FIG. 3A, the conductive material 250 couples to the tubular member 212 at an uninsulated portion of the tubular member 212. In some embodiments, the second insulating material 224 can be disposed over an outer surface of the conductive material 250 along at least a portion of its length so that the conductive material 250 is radially disposed between the second insulating material 224 and the tubular member 212. For example, as illustrated in FIG. 3B, the conductive material 250 is radially disposed between the tubular member 212 and the second insulating material 224.

The conductive material 250 can increase the electrical conductivity of the tubular member 212. The conductive material 250 can include a material that has a higher electrical conductivity than the material used to form the tubular member 212. For example, the conductive material 250 can be a gold coating while the of the tubular member 212 can be formed from Nitinol or stainless steel. By coupling a higher electrically conductive material to the tubular member 212, an electric current can more easily pass along the length of the tubular member 212 via the conductive material 250, which thus, increases the electrical conductivity of the tubular member 212.

In some embodiments, the conductive material 250 is disposed in a thin layer on the outer surface of the tubular member 212. For example, the conductive material 250 can have a thickness between about 0.05 microns to about 5 microns. Having a thickness within this range allows for the conductive material 250 to distribute current through the tubular member 212 without mechanically impacting the shaft 206 and the tubular member 212. In some embodiments, the conductive material 250 can be formed from any suitable electrically conductive material. For example, the conductive material 250 can be formed from gold, silver, copper, platinum, palladium, iridium, ruthenium, rhodium, or corresponding alloys and combinations. In various embodiments, the conductive material 250 is formed from a metallic material. Additionally or alternatively, the conductive material 250 is formed from a noble metal. In some embodiments, the conductive material 250 is coupled to the tubular member 212 by coating, plating, surface-treating, or through vapor deposition.

According to some embodiments, a conductive material 252 can be coupled to the shaft 206 along at least a portion of the length of the shaft 206. The conductive material 252 can be disposed over an outer surface of the shaft 206 so that the conductive material 252 surrounds the shaft 206. For example, as illustrated in FIG. 3E, the conductive material 252 couples to the shaft 206 so that the conductive material 252 surrounds the shaft 206. Additionally or alternatively, the conductive material 252 can be coupled to the interventional element 100. For example, as illustrated in FIG. 3F, the conductive material 252 can be disposed over an outer surface of the body 226 of the interventional element 100. In some embodiments, the conductive material 252 is disposed over the entire interventional element 100. In various embodiments, the conductive material 252 is disposed over at least a portion of the interventional element 100.

The conductive material 252 can increase the electrical conductivity of the shaft 206 and the interventional element 100. The conductive material 252 can include a material that has a higher electrical conductivity than the material used to form the shaft 206 and the interventional element 100. For example, the conductive material 252 can be formed from a gold coating while the of the shaft 206 and the interventional element 100 can be formed from Nitinol. By coupling a more electrically conductive material to the shaft 206 and the interventional element 100, an electric current can more easily pass along the length of the shaft 206 and the interventional element 100 via the conductive material 252, which thus, increases the electrical conductivity of the shaft 206 and the interventional element 100.

In some embodiments, the conductive material 252 is disposed in a thin layer on the outer surface of the shaft 206 and interventional element 100. For example, the conductive material 252 can have a thickness between about 0.05 microns to about 5 microns. Having a thickness within this range allows for the conductive material 252 to distribute current through the shaft 206 and interventional element 100 without mechanically impacting the shaft 206 and the interventional element 100. In some embodiments, the conductive material 252 can be formed from any suitable electrically conductive material. For example, the conductive material 252 can be formed gold, silver, copper, platinum, palladium, iridium, ruthenium, rhodium, or corresponding alloys and combinations. In some embodiments, the conductive material 252 is substantially the same as the conductive material 250. In various embodiments, the conductive material 252 is formed from a metallic material. Additionally or alternatively, the conductive material 252 is formed from a noble metal. In some embodiments, the conductive material 252 is coupled to the shaft 206 and the interventional element 100 by coating, plating, surface-treating, or through vapor deposition.

According to some embodiments, portions of the shaft 206 can be insulated, electrically isolating the insulated portions of the shaft 206. For example, as illustrated in FIG. 3A, the first insulating material 222 can couple to the shaft and extend distally beyond the distal end of the tubular member 212. In some embodiments, the first insulating material 222 can be disposed over an outer surface of the conductive material 252 so that the conductive material 252 is radially disposed between the first insulating material 222 and the shaft 206. For example, as illustrated in FIG. 3B, the conductive material 250 is radially disposed between the shaft 206 and the first insulating material 222. In various embodiments, the first insulating material 222 is disposed over substantially the entire shaft 206.

The first insulating material 222 can prevent electrical shortages between the shaft 206 and the tubular member 212. By electrically isolating the shaft 206 with the first insulating material 222, an electrical short can be prevented at portions where the shaft 206 is adjacent the tubular member 212. Additionally, electrically isolating portions of the shaft 206 with the first insulating material 222 can encourage current to flow to the distal portions of the interventional element 100. For example, as illustrated in FIG. 3A, the first insulating material 222 can electrically isolate portions of the shaft 206 adjacent the conductive material 250 while the distal portion of the shaft and interventional element 100 remains uninsulated. Additionally, a portion of the shaft 206 that extends distally from the distal end of the tubular member 212 can be insulated by the first insulating material 222. In these arrangements, or otherwise, current will be encouraged to flow to the distal portions of the interventional element 100, as the adjacent portions of the shaft 206 are electrically insulated.

In operation, the current generator 20 can couple to the core assembly 18 at the proximal portion 40a of the treatment device 40 and send a current through the shaft 206. This current can flow through the shaft 206 to the interventional element 100 via the conductive material 252. At the interventional element 100, the current can flow through the patient's surrounding media (e.g., blood, tissue, saline, thrombus, etc.) to the uninsulated portions of the tubular member via the conductive material 250, where the current can then flow through the tubular member 212 and return to the current generator 20.

An example method of delivering a current to the interventional element 100 will now be described. First, the treatment device 40 is positioned within a patient at the treatment site. A guidewire may be advanced through a clot material at the treatment site such that a distal terminus of the guidewire is distal of the clot material. Next, a delivery catheter 14 may be delivered over the guidewire so that a distal portion of the delivery catheter 14 is positioned at or near the clot material. In some embodiments the delivery catheter 14 may be advanced over the guidewire through the clot material such that a distal terminus of the delivery catheter 14 is distal of the clot material. With the delivery catheter 14 in position, the guidewire may be withdrawn. The interventional element 100 may then be advanced through the delivery catheter 14 in a low-profile configuration until a distal terminus 101 of the interventional element 100 is at or adjacent the distal terminus of the delivery catheter 14. The delivery catheter 14 may then be withdrawn proximally relative to the interventional element 100 to release the interventional element 100, thereby allowing the interventional element 100 to self-expand within the clot material. As the interventional element 100 expands, the interventional element 100 engages and/or secures the surrounding clot material, and in some embodiments may restore or improve blood flow through the clot material. In some embodiments, the interventional element 100 may be expanded distal of the clot material such that no portion of the interventional element 100 is engaging the clot material while the interventional element 100 is in the process of expanding toward the vessel wall. In some embodiments, the interventional element 100 is configured to expand into contact with the blood vessel wall, or the interventional element 100 may expand to a diameter that is less than that of the blood vessel lumen such that the interventional element 100 does not engage the entire circumference of the blood vessel wall.

Once the interventional element 100 has been expanded into the clot material, the interventional element 100 can grip the clot material, by virtue of its ability to mechanically interlock with the clot material as well as its ability to electrically attract, adhere, and/or attach to the clot material as a result of the delivery of electrical current to the interventional element 100. The current generator 20, which is electrically coupled to the proximal end 202 of the core assembly 18, can deliver an electrical signal to the interventional element 100 via the conductive material 252 before or after the interventional element 100 has been released from the catheter 14 into the anatomical vessel (e.g., an intracranial vessel) and/or expanded into the clot material. The electrical signal can return to the current generator 20 by flowing from the interventional element 100, through the surrounding media (e.g., blood, tissue, thrombus, etc.) to the tubular member 212 via the conductive material 250 and through the tubular member 212 to the current generator. The interventional element 100 can be left in place or manipulated within the vessel for a desired time period while the electrical signal is being delivered. In some embodiments, the electrical signal is an electrical current of between about 0-5 mA. The electrical signal can be unipolar (e.g., DC) or bipolar (e.g., AC). In various embodiments, the current or voltage level of the electrical signal can be constant, periodic, irregular, or any combination thereof. In some embodiments, the electrical signal is supplied for a duration of time between about 30 seconds to about 10 minutes. In some embodiments, the electrical signal is supplied for a duration of time of two minutes or less. Positive current delivered to the interventional element 100 can attract negatively charged constituents of the clot material, thereby enhancing the grip of the interventional element 100 on the clot material. This allows the interventional element 100 to be used to retrieve the clot material with reduced risk of losing grip on the thrombus or a piece thereof, which can migrate downstream and cause additional vessel blockages in areas of the brain that are more difficult to reach.

Once the interventional element 100 has engaged and captured the clot material, the clot material can be removed. For example, the interventional element 100 with the clot material gripped thereby, can be retracted (for example, along with the catheter 14) proximally. The catheter 14, interventional element 100, and associated clot material may then be withdrawn from the patient, optionally through one or more larger surrounding catheters. During this retraction, the interventional element 100 can grip the clot material electrically and/or electrostatically, e.g., via the application of current from a current generator 20 as discussed herein. (As used herein with reference to gripping or retrieving thrombus or other vascular/luminal material, or to apparatus for this purpose, "electrical" and its derivatives will be understood to include "electrostatic" and its derivatives.) Accordingly, the interventional element 100 can maintain an enhanced or electrically and/or electrostatically enhanced grip on the clot material during retraction. In other embodiments, the current generator 20 may cease delivery of electrical signals to the interventional element 100 prior to retraction of the interventional element 100 with respect to the vessel. In some embodiments, the interventional element 100 and clot material form a removable, integrated thrombus-device mass wherein the connection of the thrombus to the device is electrically enhanced, e.g. via the application of current as discussed herein.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A medical device comprising:
    a core assembly having a distal portion configured to be intravascularly positioned at a treatment site within a blood vessel lumen, the core assembly comprising:
    a hypotube operably coupled to a first electrical terminal, the hypotube having an insulated proximal portion, an uninsulated distal portion, and a lumen extending therethrough, the hypotube formed of a first conductive material;
    a second conductive material surrounding only the distal portion of the hypotube, wherein the second conductive material is disposed in a ring circumferentially surrounding an outer surface of the hypotube along the distal portion, the second conductive material having a higher electrical conductivity than the first conductive material;
        a pushwire operably coupled to a second electrical terminal, the pushwire extending through the hypotube lumen, wherein the pushwire is fixed with respect to the hypotube;
        an insulating material disposed radially between the hypotube and the pushwire, the insulating material extending from the proximal portion of the hypotube to the distal portion of the hypotube; and
        an interventional element coupled to a distal end of the pushwire, the interventional element having a body formed of a third conductive material and a coating of a fourth conductive material disposed over the third conductive material, the fourth conductive material having a higher electrical conductivity than the third conductive material.

2. The medical device of claim 1, wherein the second conductive material and the fourth conductive material are the same material.

3. The medical device of claim 1, wherein the second conductive material and the fourth conductive material each comprises a metallic material.

4. The medical device of claim 1, wherein the second conductive material and the fourth conductive material each comprises gold.

5. The medical device of claim 1, wherein a proximal end of the interventional element is separated from a distal end of the hypotube by a distance of at least about 1 inch.

6. The medical device of claim 1, wherein the second conductive material has a thickness of between about 0.05 microns and 5 microns.

7. The medical device of claim 1, wherein the fourth conductive material has a thickness of between about 0.05 microns and 5 microns.

8. The medical device of claim 1, wherein the insulating material is a first insulating material, the core assembly further comprising a second insulating material disposed radially around the outer surface of the hypotube along the proximal portion.

9. The medical device of claim 8, wherein the second insulating material is disposed proximal to the second conductive material.

10. A medical device comprising:
    an elongated shaft having a proximal portion configured to be electrically coupled to a current generator, an intermediate portion at least partially covered with an insulative material, and a distal portion uncovered by an insulative material;
    an elongated tubular member having a proximal portion configured to be electrically coupled to the current generator, a distal portion, and a lumen receiving the elongated shaft therethrough such that the elongated shaft is not slidable with respect to the elongated tubular member, the elongated tubular member formed of a first conductive material;
    a second conductive material circumferentially surrounding and in contact with the distal portion of the elongated tubular member, the second conductive material disposed only along the distal portion of the elongated tubular member and having a higher electrical conductivity than the first conductive material;
    an interventional element coupled to the distal portion of the elongated shaft, the interventional element comprising a body formed of a third conductive material; and
    a fourth conductive material disposed over the third conductive material, the fourth conductive material having a higher electrical conductivity than the third conductive material.

11. The medical device of claim 10, wherein the second conductive material and the fourth conductive material are the same.

12. The medical device of claim 10, wherein the second conductive material and the fourth conductive material each comprises a metallic material.

13. The medical device of claim 10, wherein the second conductive material and the fourth conductive material each comprises a noble metal.

14. The medical device of claim 10, wherein the second conductive material and the fourth conductive material each comprises gold.

15. The medical device of claim 10, wherein a proximal end of the interventional element is separated from a distal end of the elongated tubular member by a distance of at least about 1 inch.

16. The medical device of claim 10, wherein the elongated shaft extends distally beyond a distal end of the elongated tubular member.

17. The medical device of claim 10, wherein the second conductive material has a thickness of between about 0.05 microns and 5 microns.

18. The medical device of claim 10, wherein the fourth conductive material has a thickness of between about 0.05 microns and 5 microns.

19. The medical device of claim 10, wherein the interventional element is in electrical communication with the elongated shaft.

* * * * *